(12) United States Patent
Zhu

(10) Patent No.: US 8,380,301 B2
(45) Date of Patent: Feb. 19, 2013

(54) METHOD AND APPARATUS FOR DETERMINING RELATIVE POSITIONING BETWEEN NEUROSTIMULATION LEADS

(75) Inventor: Changfang Zhu, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 723 days.

(21) Appl. No.: 12/623,976

(22) Filed: Nov. 23, 2009

(65) Prior Publication Data

US 2010/0137944 A1  Jun. 3, 2010

Related U.S. Application Data

(60) Provisional application No. 61/119,669, filed on Dec. 3, 2008.

(51) Int. Cl.
*A61N 1/00* (2006.01)
(52) U.S. Cl. .......................................................... 607/2
(58) Field of Classification Search .................. 607/1–2, 607/48; 600/547
See application file for complete search history.

(56) References Cited

U.S. PATENT DOCUMENTS

| | | |
|---|---|---|
| 6,516,227 B1 | 2/2003 | Meadows et al. |
| 6,895,280 B2 | 5/2005 | Meadows et al. |
| 6,993,384 B2 | 1/2006 | Bradley et al. |
| 7,317,948 B1 | 1/2008 | King et al. |
| 7,650,184 B2 | 1/2010 | Walter |
| 7,831,307 B1 | 11/2010 | Moffitt |
| 2002/0161295 A1 | 10/2002 | Edwards et al. |
| 2003/0139781 A1 | 7/2003 | Bradley et al. |
| 2007/0168004 A1 | 7/2007 | Walter |
| 2007/0168007 A1 | 7/2007 | Kuzma et al. |
| 2008/0146926 A1 | 6/2008 | Stauch et al. |
| 2008/0221643 A1 | 9/2008 | Olson |
| 2009/0216306 A1 | 8/2009 | Barker |

FOREIGN PATENT DOCUMENTS

| | | |
|---|---|---|
| WO | WO 99/52430 A1 | 10/1999 |
| WO | WO 2008/027885 A1 | 3/2008 |

OTHER PUBLICATIONS

U.S. Appl. No. 11/557,484, System and Method for Computationally Determining Migration of Neurostimulation Leads, Inventor: Michael A. Moffit, et al., filed Nov. 7, 2006.
U.S. Appl. No. 61/030,506, Temporary Neurostimulation Lead Identification Device, Inventor: John Michael Barker, filed Feb. 21, 2008.
J. Holsheimer, et al., Optimum electrode geometry for spinal cord stimulatio: the narrow bipole and tripole, Med. Biol. Eng. Comput., 1997, 35, 493-497.
J. Holsheimer et al., Clinical Evaluation of Paresthesia Steering with a New System for Spinal Cord Stimulation, Neurosurgery, Mar. 1998, 42, 3, 541-547.

(Continued)

*Primary Examiner* — Carl H Layno
*Assistant Examiner* — Jessica Sarcione
(74) *Attorney, Agent, or Firm* — Vista IP Law Group LLP

(57) ABSTRACT

A method and medical system for operating two leads disposed adjacent tissue of a patient. A first one of a pair of electrodes respectively carried by the two leads is activated to generate an electrical field within the tissue. An electrical parameter in response to the generated electrical field is measured at a second one of the pair of electrodes. A reference electrical parameter is measured in response to the generated electrical field at a reference electrode carried by the same one of the two leads that carries the first electrode. A reference distance between the first electrode and the reference electrode is known prior to the generation of the electrical field. The ratio between the measured electrical parameter and the measured reference electrical parameter is computed, and the distance between the pair of electrodes is computed as a function of the computed ratio and the reference distance.

28 Claims, 11 Drawing Sheets

OTHER PUBLICATIONS

J.J. Struijk, et al., Transverse tripolar spinal cord stimulation: theoritical performance of a dual channel system, Med. & Biol. Eng. & Comput., 1996, 34, 273-279.

U.S. Appl. No. 11/557,484, System and Method for Computationally Determining Migration of Neurostimulation Leads, Inventor: Michael A. Moffitt, filed Nov. 7, 2006.

PCT International Search Report for PCT/US2009/065575, Applicant: Boston Scientific Neuromodulation Corporation, Form PCT/ISA/210 and 220, dated Mar. 4, 2010 (9 pages).

PCT Written Opinion of the International Search Authority for PCT/US2009/065575, Applicant: Boston Scientific Neuromodulation Corporation, Form PCT/ISA/237, dated Mar. 4, 2010 (7 pages).

PCT International Preliminary Report on Patentability (Chapter I of the Patent Cooperation Treaty) for PCT/US2009/065575, Applicant: Boston Scientific Neuromodulation Corporation, Form PCT/IB/326 and 373, dated Jun. 16, 2011 (9pages).

Struijk, J.J. et al., Transverse tripolar spinal cord stimulation: theoretical performance of a dual channel system, Med. & Biol. Eng. & Comput., 1996, 34:273-279.

Holsheimer, J. et al., Optimum electrode geometry for spinal cord stimulation: the narrow bipole and tripole, Med. Biol. Eng. Comput., 1997, 35:493-497.

Holsheimer, J. et al., Clinical Evaluation of Paresthesia Steering with a New System for Spinal Cord Stimulation, Neurosurgery, 1988, 42:541-547.

| R REF | d (mm) |
|---|---|
| 2.0 | 0.0 |
| 1.9 | 0.2 |
| 1.8 | 0.4 |
| 1.7 | 0.6 |
| 1.6 | 0.8 |
| 1.5 | 1.0 |
| 1.4 | 1.2 |
| 1.3 | 1.4 |
| 1.2 | 1.6 |
| 1.1 | 1.9 |
| 1.0 | 2.2 |
| 0.9 | 2.8 |
| 0.8 | 3.5 |
| 0.7 | 4.7 |
| 0.6 | 5.7 |
| 0.5 | 8.5 |
| 0.4 | 11.8 |
| 0.3 | 12.5 |
| 0.2 | 13.2 |
| 0.1 | 14.5 |
| 0.0 | 15.0 |

FIG. 11

METHOD AND APPARATUS FOR DETERMINING RELATIVE POSITIONING BETWEEN NEUROSTIMULATION LEADS

RELATED APPLICATION

The present application claims the benefit under 35 U.S.C. §119 to U.S. provisional patent application Ser. No. 61/119,669, filed Dec. 3, 2008. The foregoing application is hereby incorporated by reference into the present application in its entirety.

FIELD OF THE INVENTION

The present invention relates to tissue stimulation systems, and more particularly, to apparatus and methods for positioning neurostimulation leads.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Also, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes one or more stimulation leads implanted at the desired stimulation site and an implantable neurostimulator, such as an implantable pulse generator (IPG), implanted remotely from the stimulation site, but coupled either directly to the stimulation leads or indirectly to the stimulation leads via one or more lead extensions in cases where the length of the stimulation leads is insufficient to reach the IPG. Thus, electrical pulses can be delivered from the neurostimulator to the stimulation leads to stimulate the tissue and provide the desired efficacious therapy to the patient.

In the context of an SCS procedure, one or more stimulation leads are introduced through the patient's back into the epidural space, such that the electrodes carried by the leads are arranged in a desired pattern and spacing to create an electrode array. One type of commercially available stimulation leads is a percutaneous lead, which comprises a cylindrical body with ring electrodes, and can be introduced into contact with the affected spinal tissue through a Touhy-like needle, which passes through the skin, between the desired vertebrae, and into the epidural space above the dura layer. For unilateral pain, a percutaneous lead is placed on the corresponding lateral side of the spinal cord. For bilateral pain, a percutaneous lead is placed down the midline of the spinal cord, or two or more percutaneous leads are placed down the respective sides of the midline of the spinal cord, and if a third lead is used, down the midline of the special cord. After proper placement of the stimulation leads at the target area of the spinal cord, the leads are anchored in place at an exit site to prevent movement of the stimulation leads. To facilitate the location of the neurostimulator away from the exit point of the stimulation leads, lead extensions are sometimes used.

Whether lead extensions are used or not, the proximal ends of the stimulation leads exiting the spinal column are passed through a tunnel subcutaneously formed along the torso of the patient to a subcutaneous pocket (typically made in the patient's abdominal or buttock area) where a neurostimulator is implanted. The subcutaneous tunnel can be formed using a tunneling tool over which a tunneling straw may be threaded. The tunneling tool can be removed, the stimulation leads threaded through the tunneling straw, and then the tunneling straw removed from the tunnel while maintaining the stimulation leads in place within the tunnel.

The stimulation leads are then connected directly to the neurostimulator by inserting the proximal ends of the stimulation leads within one or more connector ports of the IPG or connected to lead extensions, which are then inserted into the connector ports of the IPG. The IPG can then be operated to generate electrical pulses that are delivered, through the electrodes, to the targeted tissue, and in particular, the dorsal column and dorsal root fibers within the spinal cord.

The stimulation creates the sensation known as paresthesia, which can be characterized as an alternative sensation that replaces the pain signals sensed by the patient. Intra-operatively (i.e., during the surgical procedure), the neurostimulator may be operated to test the effect of stimulation and adjust the parameters of the stimulation for optimal pain relief. The patient may provide verbal feedback regarding the presence of paresthesia over the pain area, and based on this feedback, the lead positions may be adjusted and re-anchored if necessary. A computerized programming system, such as Bionic Navigator®, available from Boston Scientific Neuromodulation Corporation, can be used to facilitate selection of the stimulation parameters. Any incisions are then closed to fully implant the system. Post-operatively (i.e., after the surgical procedure has been completed), a clinician can adjust the stimulation parameters using the computerized programming system to re-optimize the therapy.

The efficacy of SCS is related to the ability to stimulate the spinal cord tissue corresponding to evoked paresthesia in the region of the body where the patient experiences pain. Thus, the working clinical paradigm is that achievement of an effective result from SCS depends on the neurostimulation lead or leads being placed in a location (both longitudinal and lateral) relative to the spinal tissue such that the electrical stimulation will induce paresthesia located in approximately the same place in the patient's body as the pain (i.e., the target of treatment). If a lead is not correctly positioned, it is possible that the patient will receive little or no benefit from an implanted SCS system. Thus, correct lead placement can mean the difference between effective and ineffective pain therapy.

Multi-lead configurations have been increasingly used in electrical stimulation applications (e.g., neurostimulation, cardiac resynchronization therapy, etc.). In the neurostimulation application of SCS, the use of multiple leads increases the stimulation area and penetration depth (therefore coverage), as well as enables more combinations of anodic and cathodic electrodes for stimulation, such as transverse multipolar (bipolar, tripolar, or quadra-polar) stimulation, in addition to any longitudinal single lead configuration.

Several studies have demonstrated the advantage of using narrowly spaced, parallel leads placed symmetrically on both sides of the physiological midline in improving penetration and paresthesia coverage (see J. J. Struijk and J. Holsheimer Tripolar Spinal Cord Stimulation: Theoretical Performance of a Dual Channel System, Medical and Biological Engineering and Computing, Vol. 34, No. 4, 1996, pp. 273-279; J. Holsheimer, B. Nuttin, G. King, W. Wesselink, J. Gybels, and P. de Sutter, Clinical Evaluation of Paresthesia Steering with a New System for Spinal Cord Stimulation, Neurosurgery, Vol. 42, No. 3, 1998, pp. 541-549; Holsheimer J., Wesselink, W. A., Optimum Electrode Geometry for Spinal Cord Stimulation: the Narrow Bipole and Tripole, Medical and Biological Engineering and Computing, Vol. 35, 1997, pp. 493-497).

For example, to produce the feeling of paresthesia without inducing discomfort or involuntary motor movements within the patient, it is often desirable to preferentially stimulate nerve fibers in the dorsal column (DC) nerve fibers, which primarily include sensory nerve fibers, over nerve fibers in the dorsal root (DR) nerve fibers, which include both sensory nerve fibers and motor reflex nerve fibers. In order to stimulate the DC nerve fibers, while guarding against the stimulation of the DR nerve fibers, a transverse tripolar lead arrangement may activate anodes that flank a single cathode in a medial-lateral electrical field, with the single cathode providing the stimulation energy for the DC fibers, while the flanking anodes guarding against the over-stimulation of the DR fibers, thereby increasing the therapeutic range of SCS for stimulating the desired DC fibers, while reducing the unwanted side effect of stimulating DR fibers Thus, in a multi-lead system, more particularly a system using multiple percutaneous leads, it is desired that two or more leads are placed parallel in close proximity to each other. During the lead implantation, the leads are placed closely at the surgeon's best effort. Fluoroscopy images are usually acquired after lead insertion to verify the placement and proximity of the leads, and a revision/correction can be made if necessary. Since the leads are ultimately placed in three-dimensional space, two-dimensional fluoroscopic views (e.g., in the context of SCS, an anteroposterior (AP) view and a lateral view) are used to check the lead proximity.

However, fluoroscopic imaging requires a bulky instrument, which limits its use in the operating room. Thus, sometimes, only an AP view is acquired, while a lateral view is optional and its acquisition depends on the preference of the surgeon. When only an AP view is acquired, it is usually assumed that there is no offset of the leads on the lateral view. However, in some cases, the visual estimate of lead proximity from an AP fluoroscopic image may incorrectly indicate that the leads are in close proximity, when in fact, the leads may be actually be quite separated from each other; something that may only be detected from a lateral fluoroscopic image of the leads. If such lead placement is not detected in a timely manner before the system is fully implanted, it may result in inefficient therapy and possibly require a second surgery for lead revision.

In addition, when programming a transverse tripolar system, knowing which electrode is in the middle of the medio-lateral electrode arrangement is absolutely critical to selecting the cathode that provides the stimulation, as well as selecting the anodes that provide the guarding function. Once the leads have been implanted, identifying the middle stimulation lead can be challenging.

Oftentimes, multiple leads may extend from the spinal region of the patient. For example, multiple percutaneous leads may be implanted within the patient adjacent the spinal cord. Because the programming of the IPG will depend upon the physical locations of the electrodes relative to the patient's spinal cord (especially in the case of a tripolar system as just described), the proximal ends of the leads may be labeled before passing them through the tunneling straw, so that the surgeon can keep track of which set of electrodes is connected to which connector port on the implanted IPG (which may include three ports for a medio-lateral electrode arrangement).

One technique used by surgeons to identify the leads is to tie sutures around the proximal ends of the leads prior to introducing them through the tunneling straw; for example, one suture around a first lead, two sutures around a second lead, three sutures around a third lead, etc. Once the proximal ends of the leads exit the tunneling straw, the surgeon can then identify each lead (and thus the corresponding electrodes) by the number of sutures tied to the respective lead, thereby allowing the lead to be connected to the correct port on the IPG.

While this technique can be successfully employed to identify leads, it considerably extends the length of the surgery time, which is undesirable. In some cases, the identification features, such as different colors or markings, can be incorporated into the proximal ends of the leads, such that the leads can be identified as they exit the tunneling straw. Even with the use of visual identifiers, however, the proximal ends of the leads can still be inserted into the incorrect connector ports, or the distal ends of the leads may have been mixed up during lead insertion, and therefore, the visual identifiers will not correspond to their intended electrodes. If the leads are inserted into the incorrect connector ports, intra-operative testing of the lead placement may be compromised. Additional surgical time may be wasted to identify and correct the connection problem. If the errors remain unidentified, the patient may leave the operating room with the leads incorrectly connected. During post-operative fitting, additional time may then be lost identifying and compensating for leads that are not in the proper connector ports. This ultimately can result in sub-optimal therapy.

Another technique that can be used to identify the leads is to individually activate stimulation for each lead and request the patient to provide paresthesia feedback (e.g., feeling from left, right, or both sides of the body) in order to determine the medio-lateral order of the leads. This could be time-consuming and may become confusing if the middle lead is placed laterally to the spinal cord physiological midline. Also, this conventional method may not be able to reveal the relative proximity of the two lateral leads absent a fluoroscopic procedure.

Additionally, in the case where multiple percutaneous leads are used to construct the medio-lateral electrode arrangement, knowing the relative proximity of the lateral leads to the middle lead is also helpful in sculpting the current/voltage applied to each guarding anode. Furthermore, the leads may not be oriented perfectly parallel, but rather tilted at an angle. In such cases, knowing the proximity (and in particular, the separation between two adjacent cross-lead electrodes) and relative orientation of the leads to each other may be critical to sculpting the stimulation current/voltage applied to each active electrode.

There, thus, remains a need for a quick, effective, and low-cost method for determining the relative proximity and orientation between two or more neurostimulation leads and/or identifying the middle lead of a tri-lead system.

SUMMARY OF THE INVENTION

In accordance with a first aspect of the present inventions, a method of operating two leads disposed adjacent tissue of a patient is provided. The method comprises activating one of a pair of electrodes respectively carried by the two leads to generate an electrical field within the tissue (e.g. spinal cord tissue). The method further comprises measuring an electrical parameter (e.g., a field potential or an impedance) in response to the generated electrical field at the other of the pair of electrodes, and measuring a reference electrical parameter (e.g., a field potential or an impedance) in response to the generated electrical field at a reference electrode carried by the same one of the two leads that carries the one electrode. For the purposes of this specification, the electrical field measured at the other electrode and reference electrode may be generated by the activated electrode at the same time or may be generated at different times. A reference distance between the one electrode and the reference electrode is known prior to the generation of the electrical field. One optional method further comprises determining a longitudinal stagger between the two leads, and selecting the pair of electrodes having the least amount of longitudinal stagger based on the determined longitudinal stagger.

The method further comprises computing a ratio between the measured electrical parameter and the measured reference electrical parameter, and computing a distance between the pair of electrodes as a function of the computed ratio and the reference distance. In one method, the ratio may be computed by dividing the measured electrical parameter by the measured reference electrical parameter, in which case, the function may be a division (e.g., if the electrical parameter is a field potential) or multiplication (e.g., if the electrical parameter is an impedance) of the reference distance by the computed ratio. In another method, the ratio may be computed by dividing the measured reference electrical parameter by the measured electrical parameter, in which case, the function may be a multiplication (e.g., if the electrical parameter is a field potential) or division (e.g., if the electrical parameter is an impedance) of the reference distance by the computed ratio.

One method further comprises determining the relative positioning (e.g., distance and/or angle) between the two leads at least partially based on the computed distance. In this case, the method may further comprise activating one of another pair of electrodes respectively carried by the two leads to generate another electrical field within the tissue, repeating the electrical parameter measuring for the remaining one of the other pair of electrodes, repeating the reference electrical parameter measuring for another reference electrode, and repeating the ratio computing and distance computing steps to determine another distance between the other pair of electrodes.

The method may further comprise plotting the distances, and fitting a lead model to the plotted distances, wherein the relative positioning between the two leads is determined based on the fitted lead model. In another method, three leads are operated, with one being a middle lead and the remaining pair of leads flanking the middle lead. In this case, the method may further comprise identifying the middle lead based on the computed distance. The method may further comprise displaying the relative positioning of the two leads based on the computed distance and/or programming a neurostimulator with a plurality of stimulation parameters based on the computed distance.

In accordance with a second aspect of the present inventions, a medical system is provided. The medical system comprises a first and second leads configured for being placed adjacent tissue of a patient. The first lead carries a first electrode and a reference electrode, and the second lead carries a second electrode. The medical system further comprises a controller configured for activating the first electrode to generate an electrical field within the tissue. The medical system further comprises monitoring circuitry configured for measuring an electrical parameter (e.g., a field potential or impedance) in response to the generated electrical field at the second electrode, and measuring a reference electrical parameter (e.g., a field potential or impedance) in response to the generated electrical field at the reference electrode. A reference distance between the first electrode and the reference electrode is known prior to generation of the electrical field. In an optional embodiment, processor(s) is configured for determining a longitudinal stagger between the two leads, and selecting the first and second electrodes having the least amount of longitudinal stagger based on the determined longitudinal stagger.

The medical system further comprises at least one processor configured for computing a ratio between the measured electrical parameter and the measured reference electrical parameter, and computing a distance between the first and second electrodes as a function of the computed ratio and the reference distance. As one example, the processor(s) may be configured for computing ratio by dividing the measured electrical parameter by the measured reference electrical parameter, in which case, the function may be a division (e.g., if the electrical parameter is a field potential) or multiplication (e.g., if the electrical parameter is an impedance) of the reference distance by the computed ratio. As another example, the processor(s) may be configured for computing ratio by dividing the measured reference electrical parameter by the measured electrical parameter, in which case, the function may be a multiplication (e.g., if the electrical parameter is a field potential) or division (e.g., if the electrical parameter is an impedance) of the reference distance by the computed ratio. In one embodiment, the processor(s) is configured for determining the relative positioning (e.g., distance and/or angle) between the two leads at least partially based on the computed distance.

In another embodiment, the first lead carries a third electrode and another reference electrode, and the second lead carries a fourth electrode. In this case, the controller may be configured for activating the third electrode to generate another electrical field within the tissue, the monitoring circuitry may be configured for repeating the electrical parameter measuring and the reference electrical parameter measuring with respect to the fourth electrode and the other reference electrode, and the processor(s) may be configured for performing the ratio computing and distance computing to determine another distance between the third and fourth electrodes. The processor(s) may also be configured for plotting the first and second distances, fitting a straight line or a curve to the first and second plotted distances, and determining the relative positioning between the two leads based on the fitted straight line or curve.

In another embodiment, the medical system further comprises a third lead configured for being placed adjacent tissue of a patient, with the first, second, and third leads being configured to be arranged as a middle lead and two leads flanking the middle leads. In this case, the processor(s) is configured for identifying the middle lead based on the computed distance.

In an optional embodiment, the medical system further comprises a monitor configured for displaying the relative positioning of the two leads based on the computed distance. In another optional embodiment, the medical system further comprises a neurostimulator and an external device. In this case, the controller may be contained within the implantable device, and one or more of the processors may be contained within the external device.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 11 is a look-up table of cross-lead/intra-lead field potential ratios and corresponding electrode separation distance values used by the CP to determine the relative positioning of the neurostimulation leads shown of FIG. 8.

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
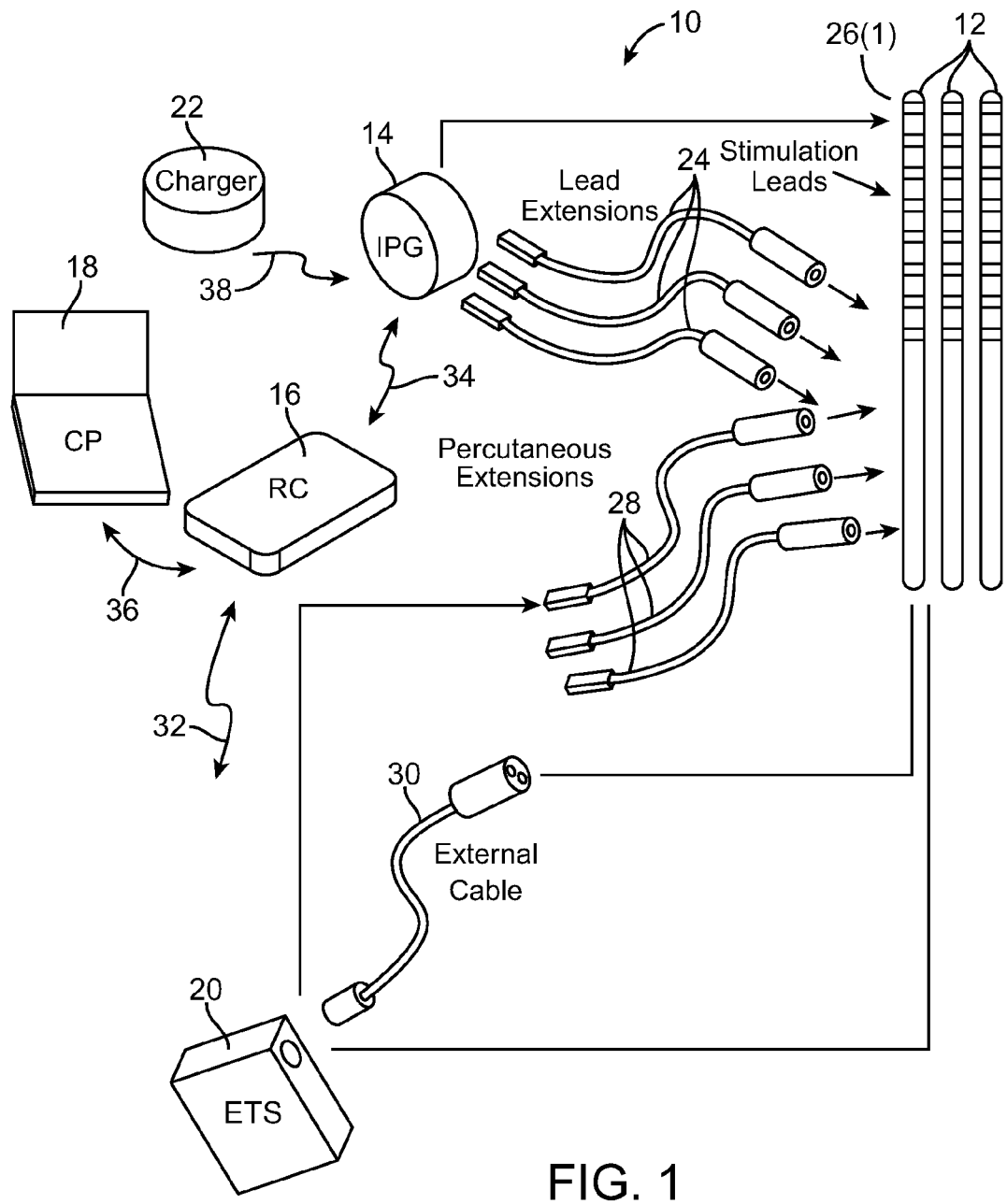
FIG. 1 is plan view of one embodiment of a spinal cord stimulation (SCS) system arranged in accordance with the present inventions.

Turning first to FIG. 1, an exemplary SCS system 10 generally comprises a plurality of percutaneous leads 12 (in this case, three), an implantable pulse generator (IPG) 14, an external remote control (RC) 16, a Clinician's Programmer (CP) 18, an External Trial Stimulator (ETS) 20, and an external charger 22.

The IPG 14 is physically connected via three lead extensions 24 to the stimulation lead 12, which carry a plurality of electrodes 26 arranged in an array. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters. The IPG 14 and stimulation leads 12 can be provided as an implantable neurostimulation kit, along with, e.g., a hollow needle, a stylet, a tunneling tool, and a tunneling straw. Further details discussing implantable kits are disclosed in U.S. Application Ser. No. 61/030,506, entitled "Temporary Neurostimulation Lead Identification Device," which is expressly incorporated herein by reference.

The ETS 20 may also be physically connected via percutaneous lead extensions 28 or external cable 30 to the stimulation lead 12. The ETS 20, which has similar pulse generation circuitry as the IPG 14, also delivers electrical stimulation energy in the form of a pulse electrical waveform to the electrode array 26 in accordance with a set of stimulation parameters. The major difference between the ETS 20 and the IPG 14 is that the ETS 20 is a non-implantable device that is used on a trial basis after the stimulation lead 12 has been implanted and prior to implantation of the IPG 14, to test the responsiveness of the stimulation that is to be provided. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation lead 12 is implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
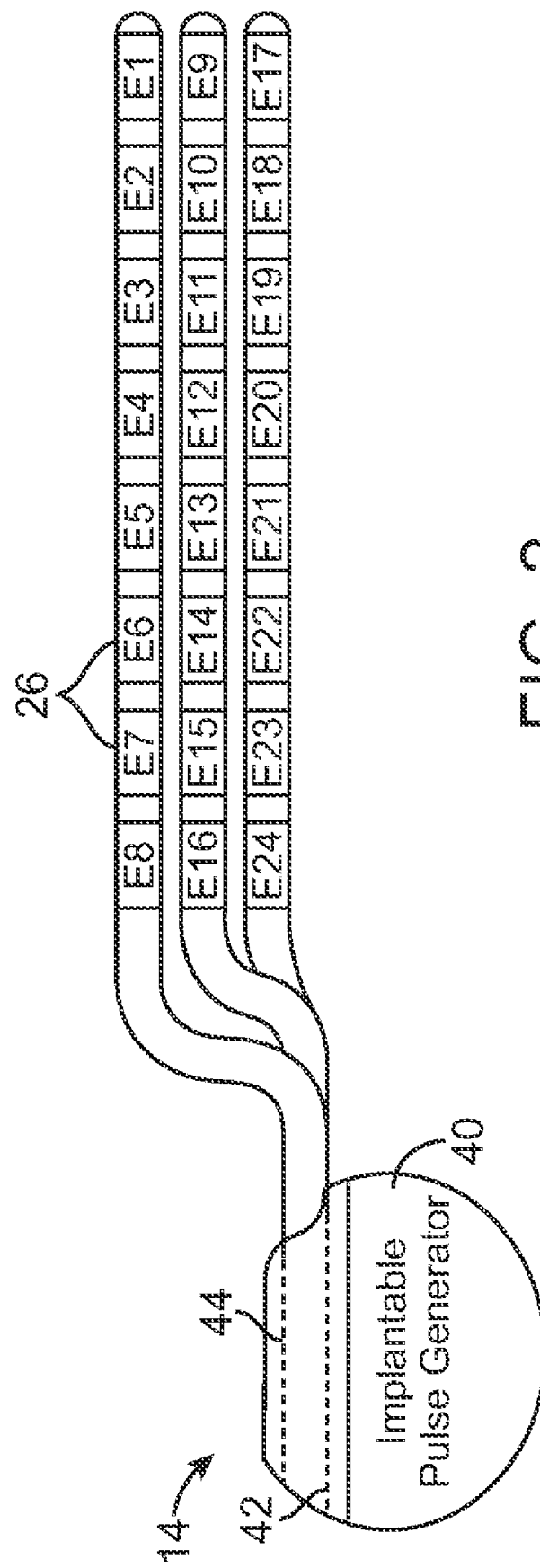
FIG. 2 is a plan view of an implantable pulse generator (IPG) and another embodiment of a percutaneous stimulation lead used in the SCS system of FIG. 1.

Referring now to FIG. 2, the external features of the stimulation leads 12 and the IPG 14 will be briefly described. Each of the stimulation leads 12 has eight electrodes 26 (respectively labeled E1-E8, E9-E16, and E17-E24). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

The IPG 14 comprises an outer case 40 for housing the electronic and other components (described in further detail below). The outer case 40 is composed of an electrically conductive, biocompatible material, such as titanium, and forms a hermetically sealed compartment wherein the internal electronics are protected from the body tissue and fluids. In some cases, the outer case 40 may serve as an electrode. The IPG 14 further comprises a connector 42 to which the proximal ends of the stimulation leads 12 mate in a manner that electrically couples the electrodes 26 to the internal electronics (described in further detail below) within the outer case 40. To this end, the connector 42 includes three ports 44 (only one shown in phantom) for receiving the proximal ends of the three percutaneous leads 12. In the case where the lead extensions 24 are used, the ports 44 may instead receive the proximal ends of such lead extensions 24.

As will be described in further detail below, the IPG 14 includes pulse generation circuitry that provides electrical stimulation energy to the electrodes 26 in accordance with a set of parameters. Such parameters may comprise electrode combinations, which define the electrodes that are activated as anodes (positive), cathodes (negative), and turned off (zero), and electrical pulse parameters, which define the pulse amplitude (measured in milliamps or volts depending on whether the IPG 14 supplies constant current or constant voltage to the electrodes), pulse duration (measured in microseconds), pulse rate (measured in pulses per second), and pulse shape.

With respect to the pulse patterns provided during operation of the SCS system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case 40, so that the electrical current has a path from the energy source contained within the IPG case 40 to the tissue and a sink path from the tissue to the energy source contained within the case. Electrical energy may be transmitted to the tissue in a monopolar or multipolar (e.g., bipolar, tripolar, etc.) fashion.

Monopolar delivery occurs when a selected one or more of the lead electrodes 26 is activated along with the case 40 of the IPG 14, so that electrical energy is transmitted between the selected electrode 26 and case 40. Monopolar delivery may also occur when one or more of the lead electrodes 26 are activated along with a large group of lead electrodes located remotely from the one or more lead electrodes 26 so as to create a monopolar effect; that is, electrical energy is conveyed from the one or more lead electrodes 26 in a relatively isotropic manner. Bipolar delivery occurs when two of the lead electrodes 26 are activated as anode and cathode, so that electrical energy is transmitted between the selected electrodes 26. Tripolar delivery occurs when three of the lead electrodes 26 are activated, two as anodes and the remaining one as a cathode, or two as cathodes and the remaining one as an anode.

Figure 3:
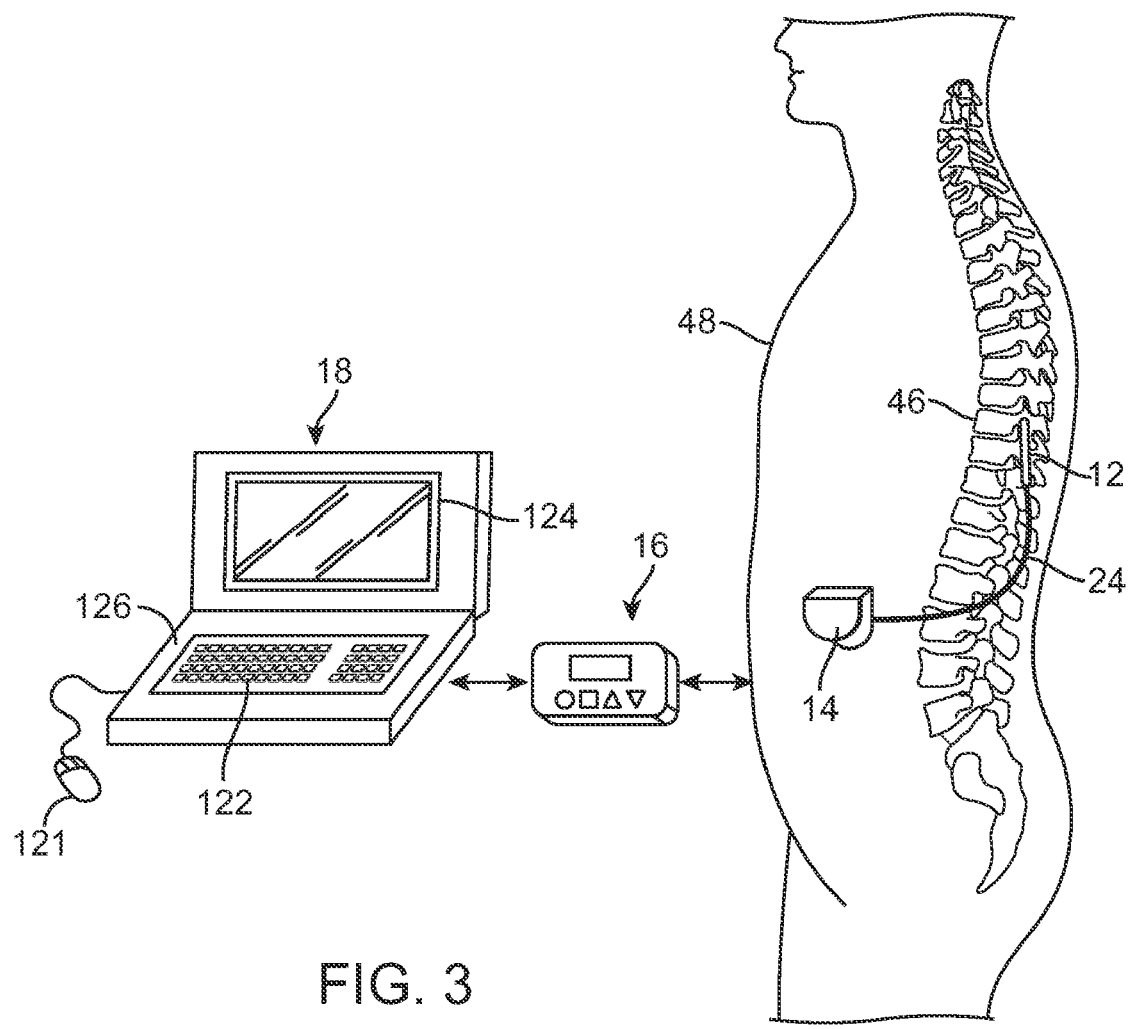
FIG. 3 is a plan view of the SCS system of FIG. 1 in use with a patient.

Referring to FIG. 3, the stimulation leads 12 are implanted within the spinal column 46 of a patient 48. The preferred placement of the stimulation leads 12 is adjacent, i.e., resting near, or upon the dura, adjacent to the spinal cord area to be stimulated. Due to the lack of space near the location where the stimulation leads 12 exit the spinal column 46, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the stimulation leads 12. As there shown, the CP 18 communicates with the IPG 14 via the RC 16. While the stimulation leads 12 are illustrated as being implanted near the spinal cord area of a patient, the stimulation leads 12 may be implanted anywhere in the patient's body, including a peripheral region, such as a limb, or the brain. It can be appreciated from the foregoing that the three percutaneous leads 12 allow three columns of electrodes 26 (in this case, E1-E8, E9-E16, and E17-E24) can be located along the spinal cord tissue. In this manner, three adjacent electrodes 26 from the respective electrode columns can be transversely placed across spinal cord tissue to form a medio-lateral electrode arrangement, with one of the electrodes 26 being used as a middle electrode, and the remaining two electrodes 26 being used as flanking electrodes. After implantation, the IPG 14 is used to provide the therapeutic stimulation under control of the patient.

Figure 4:
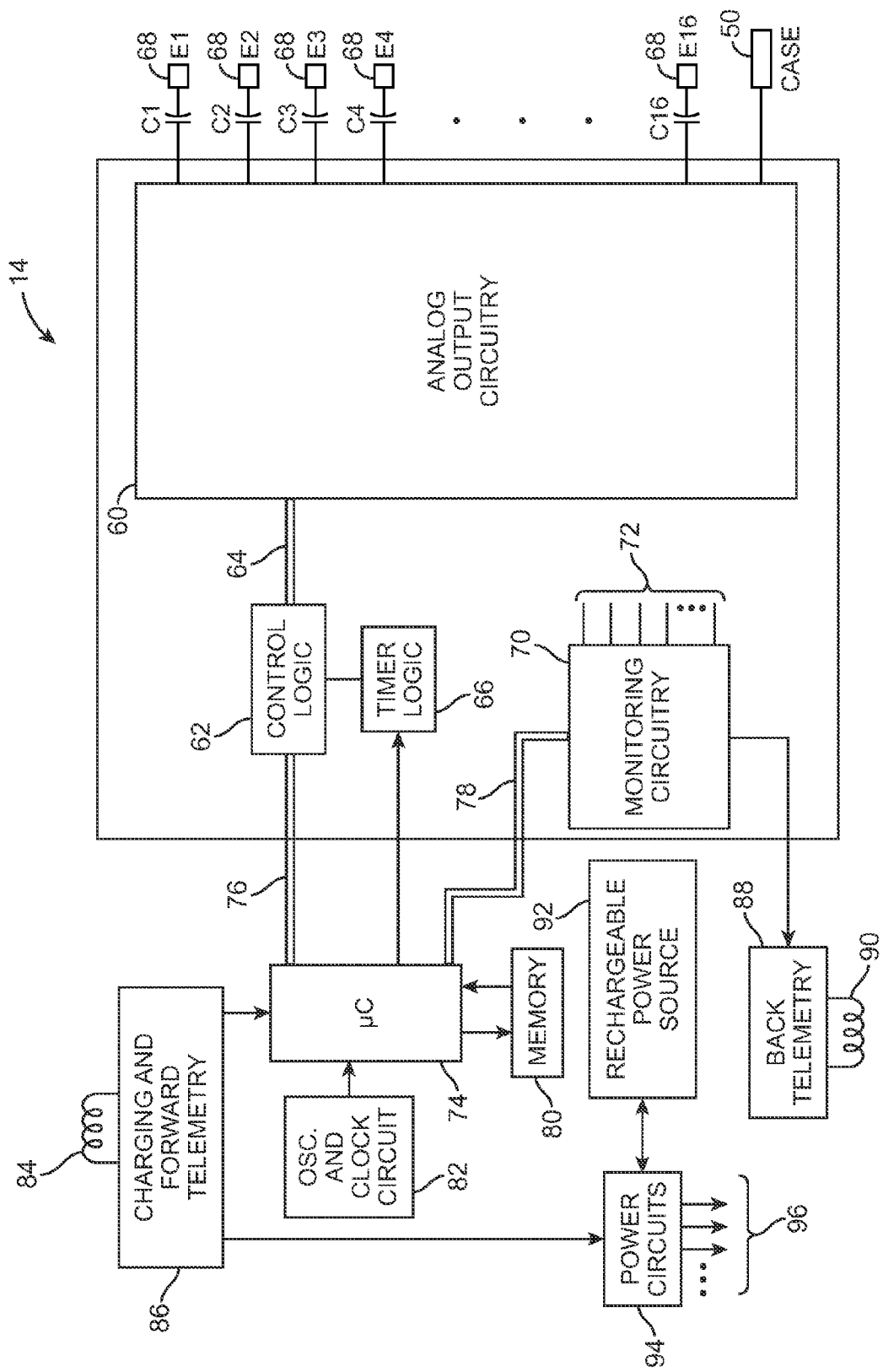
FIG. 4 is a block diagram of the internal components of the IPG of FIG. 1.

Turning next to FIG. 4, the main internal components of the IPG 14 will now be described. The IPG 14 includes stimulation output circuitry 60 configured for generating electrical stimulation energy in accordance with a defined pulsed waveform having a specified pulse amplitude, pulse rate, pulse width, pulse shape, and burst rate under control of control logic 62 over data bus 64. Control of the pulse rate and pulse width of the electrical waveform is facilitated by timer logic circuitry 66, which may have a suitable resolution, e.g., 10 µs. The stimulation energy generated by the stimulation output circuitry 60 is output via capacitors C1-C16 to electrical terminals 68 corresponding to the electrodes 26.

The analog output circuitry 60 may either comprise independently controlled current sources for providing stimulation pulses of a specified and known amperage to or from the electrical terminals 68, or independently controlled voltage sources for providing stimulation pulses of a specified and known voltage at the electrical terminals 68 or to multiplexed current or voltage sources that are then connected to the electrical terminals 68. The operation of this analog output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 further comprises monitoring circuitry 70 for monitoring the status of various nodes or other points 72 throughout the IPG 14, e.g., power supply voltages, temperature, battery voltage, and the like. Notably, the electrodes 26 fit snugly within the epidural space of the spinal column, and because the tissue is conductive, electrical measurements can be taken from the electrodes 26. Significantly, the monitoring circuitry 70 is configured for taking such electrical measurements, so that, as will be described in further detail below, the CP 18 can automatically determine the relative positioning between the leads 12, as well as to identify the middle lead 12 in the case where a tripolar lead arrangement is utilized. In the illustrated embodiment, the electrical measurements taken by the monitoring circuitry 70 for the purpose of identifying the connected lead bodies, are field potentials or other electrical parameters (e.g., current and/or impedance) that may be used to derive the field potential. The monitoring circuitry 70 may also measure impedance at each electrode 26 in order to determine the coupling efficiency between the respective electrode 26 and the tissue and/or to facilitate fault detection with respect to the connection between the electrodes 26 and the analog output circuitry 60 of the IPG 14.

Electrical data can be measured using any one of a variety means. For example, the electrical data measurements can be made on a sampled basis during a portion of the time while the electrical stimulus pulse is being applied to the tissue, or immediately subsequent to stimulation, as described in U.S. patent application Ser. No. 10/364,436, which has previously been incorporated herein by reference. Alternatively, the electrical data measurements can be made independently of the electrical stimulation pulses, such as described in U.S. Pat. Nos. 6,516,227 and 6,993,384, which are expressly incorporated herein by reference.

The IPG 14 further comprises processing circuitry in the form of a microcontroller 74 that controls the control logic 62 over data bus 76, and obtains status data from the monitoring circuitry 70 via data bus 78. The microcontroller 74 additionally controls the timer logic 66. The IPG 14 further comprises memory 80 and an oscillator and clock circuit 82 coupled to the microcontroller 74. The microcontroller 74, in combination with the memory 80 and oscillator and clock circuit 82, thus comprise a microprocessor system that carries out a program function in accordance with a suitable program stored in the memory 80. Alternatively, for some applications, the function provided by the microprocessor system may be carried out by a suitable state machine.

Thus, the microcontroller 74 generates the necessary control and status signals, which allow the microcontroller 74 to control the operation of the IPG 14 in accordance with a selected operating program and parameters. In controlling the operation of the IPG 14, the microcontroller 74 is able to individually generate electrical pulses at the electrodes 26 using the analog output circuitry 60, in combination with the control logic 62 and timer logic 66, thereby allowing each electrode 26 to be paired or grouped with other electrodes 26, including the monopolar case electrode, and to control the polarity, amplitude, rate, and pulse width through which the current stimulus pulses are provided.

The IPG 14 further comprises an alternating current (AC) receiving coil 84 for receiving programming data (e.g., the operating program and/or stimulation parameters) from the RC 16 in an appropriate modulated carrier signal, and charging and forward telemetry circuitry 86 for demodulating the carrier signal it receives through the AC receiving coil 84 to recover the programming data, which programming data is then stored within the memory 80, or within other memory elements (not shown) distributed throughout the IPG 14.

The IPG 14 further comprises back telemetry circuitry 88 and an alternating current (AC) transmission coil 90 for sending informational data (including the field potential and impedance data) sensed through the monitoring circuitry 70 to the RC 16. The back telemetry features of the IPG 14 also allow its status to be checked. For example, any changes made to the stimulation parameters are confirmed through back telemetry, thereby assuring that such changes have been correctly received and implemented within the IPG 14. Moreover, upon interrogation by the RC 16, all programmable settings stored within the IPG 14 may be uploaded to the RC 16.

The IPG 14 further comprises a rechargeable power source 92 and power circuits 94 for providing the operating power to the IPG 14. The rechargeable power source 92 may, e.g., comprise a lithium-ion or lithium-ion polymer battery. The rechargeable battery 92 provides an unregulated voltage to the power circuits 94. The power circuits 94, in turn, generate the various voltages 96, some of which are regulated and some of which are not, as needed by the various circuits located within the IPG 14. The rechargeable power source 92 is recharged using rectified AC power (or DC power converted from AC power through other means, e.g., efficient AC-to-DC converter circuits) received by the AC receiving coil 84. To recharge the power source 92, an external charger (not shown), which generates the AC magnetic field, is placed against, or otherwise adjacent, to the patient's skin over the implanted IPG 14. The AC magnetic field emitted by the external charger induces AC currents in the AC receiving coil 84. The charging and forward telemetry circuitry 86 rectifies the AC current to produce DC current, which is used to charge the power source 92. While the AC receiving coil 84 is described as being used for both wirelessly receiving communications (e.g., programming and control data) and charging energy from the external device, it should be appreciated that the AC receiving coil 84 can be arranged as a dedicated charging coil, while another coil, such as coil 90, can be used for bi-directional telemetry.

It should be noted that the diagram of FIG. 4 is functional only, and is not intended to be limiting. Those of skill in the art, given the descriptions presented herein, should be able to readily fashion numerous types of IPG circuits, or equivalent circuits, that carry out the functions indicated and described. It should be noted that rather than an IPG for the neurostimulator, the SCS system 10 may alternatively utilize an implantable receiver-stimulator (not shown) connected to the stimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 5:
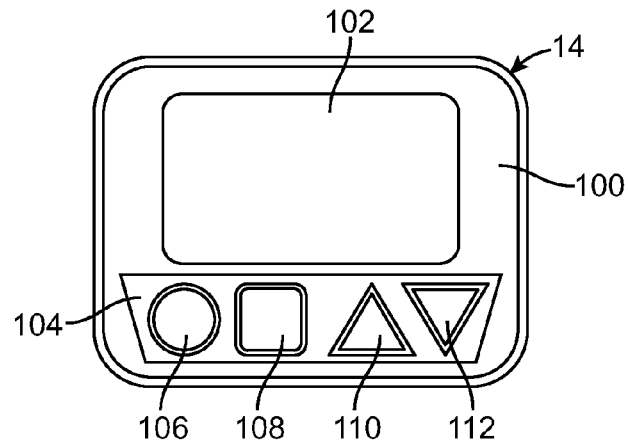
FIG. 5 is a plan view of a remote control that can be used in the SCS system of FIG. 1.

Referring now to FIG. 5, one exemplary embodiment of an RC 16 will now be described. As previously discussed, the RC 16 is capable of communicating with the IPG 14, CP 18, or ETS 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touchscreen capabilities. The button pad 104 includes a multitude of buttons 106, 108, 110, and 112, which allow the IPG 14 to be turned ON and OFF, provide for the adjustment or setting of stimulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 106 to switch between screen displays and/or parameters. The buttons 110 and 112 serve as up/down buttons that can be actuated to increase or decrease any of stimulation parameters of the pulse generated by the IPG 14, including pulse amplitude, pulse width, and pulse rate.

Figure 6:
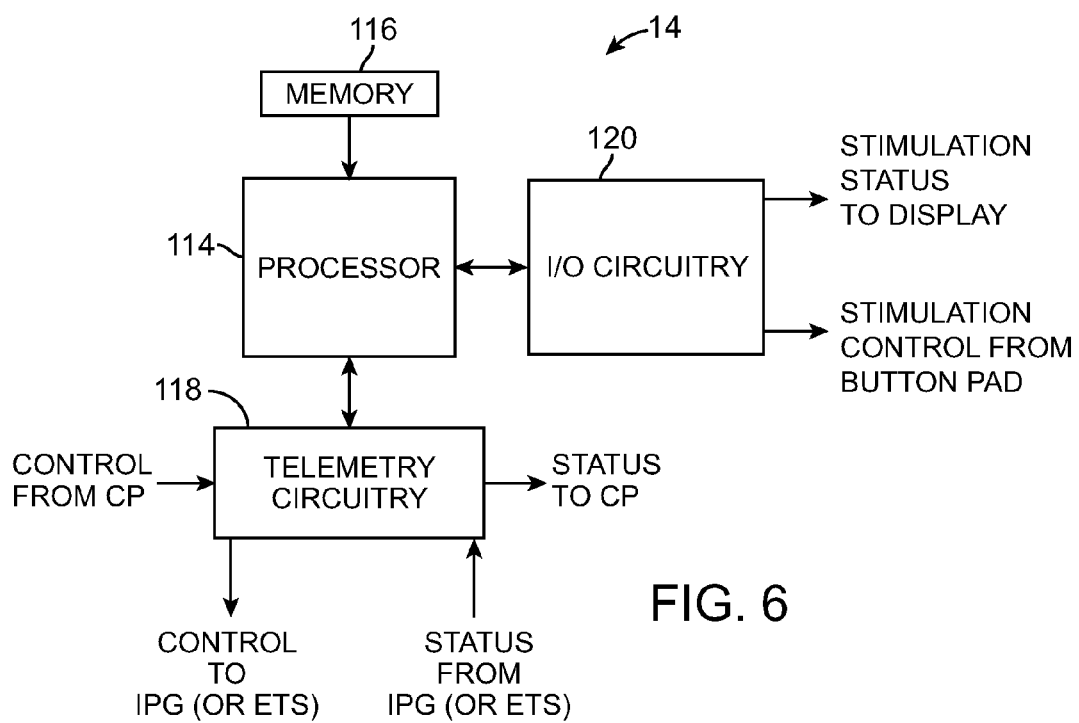
FIG. 6 is a block diagram of the internal componentry of the remote control of FIG. 5.

Referring to FIG. 6, the internal components of an exemplary RC 16 will now be described. The RC 16 generally includes a processor 114 (e.g., a microcontroller), memory 116 that stores an operating program for execution by the processor 114, and telemetry circuitry 118 for transmitting control data (including stimulation parameters and requests to provide status information) to the IPG 14 (or ETS 20) and receiving status information (including the measured electrical data) from the IPG 14 (or ETS 20) via link 34 (or link 32) (shown in FIG. 1), as well as receiving the control data from the CP 18 and transmitting the status data to the CP 18 via link 36 (shown in FIG. 1). The RC 16 further includes input/output circuitry 120 for receiving stimulation control signals from the button pad 104 and transmitting status information to the display screen 102 (shown in FIG. 5). Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the physician or clinician to readily determine the desired stimulation parameters to be programmed into the IPG 14, as well as the RC 16. Thus, modification of the stimulation parameters in the programmable memory of the IPG 14 after implantation is performed by a clinician using the CP 18, which can directly communicate with the IPG 14 or indirectly communicate with the IPG 14 via the RC 16. That is, the CP 18 can be used by the physician or clinician to modify operating parameters of the electrode array 26 near the spinal cord.

As shown in FIG. 3, the overall appearance of the CP 18 is that of a laptop personal computer (PC), and in fact, may be implemented using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 (or ETS 20) to allow the optimum stimulation parameters to be determined based on patient feedback and for subsequently programming the IPG 14 (or ETS 20) with the optimum stimulation parameters.

Figure 7:
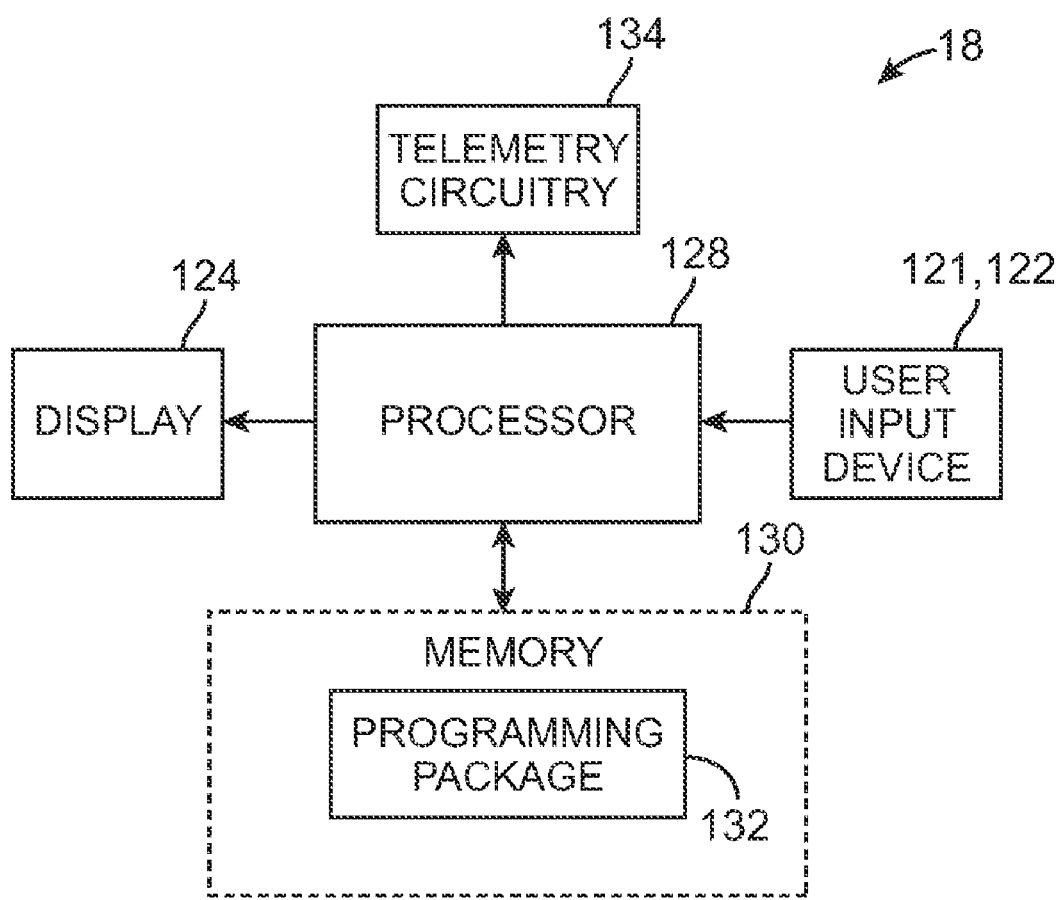
FIG. 7 is a block diagram of the components of a clinician's programmer that can be used in the SCS system of FIG. 1.

To allow the clinician to perform these functions, the CP 18 includes a mouse 121, a keyboard 122, and a programming display screen 124 housed in a case 126. It is to be understood that in addition to, or in lieu of, the mouse 121, other directional programming devices may be used, such as a joystick, or directional keys included as part of the keys associated with the keyboard 122. As shown in FIG. 7, the CP 18 generally includes a processor 128 (e.g., a central processor unit (CPU)) and memory 130 that stores a stimulation programming package 132, which can be executed by the processor 128 to allow a clinician to program the IPG 14 (or ETS 20) and RC 16. The CP 18 further includes telemetry circuitry 134 for downloading stimulation parameters to the RC 16 and uploading stimulation parameters already stored in the memory 116 of the RC 16 via link 36 (shown in FIG. 1). The telemetry circuitry 134 is also configured for transmitting the control data (including stimulation parameters and requests to provide status information) to the IPG 14 (or ETS 20) and receiving status information (including the measured electrical data) from the IPG 14 (or ETS 20) indirectly via the RC 16.

The CP 18 is configured for automatically determining the relative positioning (e.g., the separation and/or tilt angle) of the percutaneous leads 12 by taking one or more cross-lead electrical field measurements and comparing these measurements to reference intra-lead electrical field measurements to determine the separation distance between pairs of cross-lead electrodes. In the embodiment described below, field potential measurements are taken, although other types of measurements, such as impedance measurements, can alternatively be taken.

Figure 8:
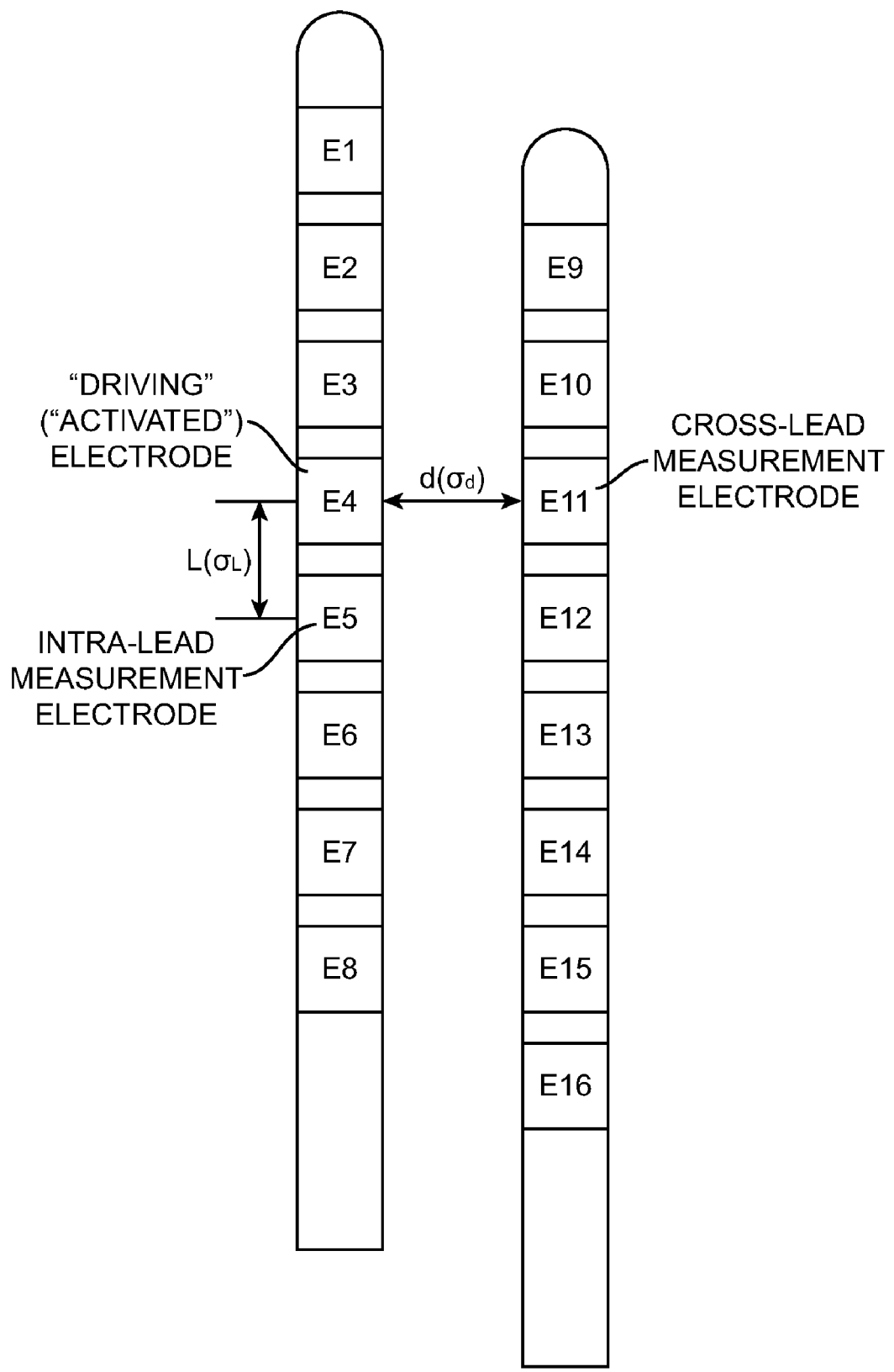
FIG. 8 is a plan view of two neurostimulation leads used in the SCS system of FIG. 1.

With reference to FIG. 8, the CP 18 can determine the separation distances between any pair of cross-lead electrodes (e.g., electrodes E4 and E11) by activating one electrode (e.g., electrode E4) of the respective electrode pair to generate an electrical field within the tissue, measuring an electrical parameter (in this case, the field potential) at the other electrode (e.g., electrode E11) of the electrode pair, and measuring an electrical parameter (in this case, the field potential) at an electrode located on the same lead (e.g., electrode E5) in which the activated electrode is located. Notably, any electrode on the same lead as the activated electrode can be used as long as the distance between the two electrodes is known. The electrical field can be monopolar (i.e., generated between the activated electrode and the case of the IPG) or bipolar (i.e., generated between the activated electrode and a return electrode on a lead).

Notably, for an electrical field resulting from a constant point current source in a medium of conductivity $\sigma$, the measured field potential is inversely proportionate to the product of the distance and the conductivity between the "driving" (or "active") electrode and the measurement electrode, and can be expressed as follows: $FP\_e_m(E_n) \propto 1/r\sigma$, where $FP\_e_m(E_n)$ is the magnitude of the measured field potential generated at an activated electrode $e_m$ and measured at an electrode $E_n$, r is the distance between the activated electrode $e_m$ and the measurement electrode $E_n$, $\sigma$ is the conductivity between the active electrode $e_m$ and the measurement electrode $E_n$, and m and n are respectively the electrode numbers.

Since the separation distance between two intra-lead electrodes (e.g., electrodes E4 and E5) is fixed and known, it may serve as a reference for the estimate of separation between two cross-lead electrodes (e.g., electrodes E4 and E11). For the same activated electrode (e.g., electrode E4), the ratio of the field potential FP measured from a cross-lead electrode (e.g., electrode E11), and the field potential FP measured from an intra-lead electrode (e.g., electrode E5) can be expressed as follows:

$$R = FP\_e_4(E_{11})/FP\_e_4(E_5) = L\sigma_L/d\sigma_d \qquad [2]$$

where L is the separation distance between the activated electrode and the intra-lead measurement electrode, d is the separation distance between the activated electrode and cross-lead measurement electrode, $\sigma_L$ is the intra-lead conductivity (i.e., the conductivity between the activated electrode and the intra-lead measurement electrode), and $\sigma_d$ is the cross-lead conductivity (i.e., the conductivity between the activated electrode and the cross-lead measurement electrode).

If the conductivities $\sigma_L$ and $\sigma_d$ or the ratio of conductivities $\sigma_L$ and $\sigma_d$ (i.e., $\sigma_L/\sigma_d$) are known, the ratio R is then a function of the separation distance d between the activated electrode and the cross-lead measurement electrode (denoted R(d)). If the relationship between the ratio R and separation distance d is determined, monotonic, and known, the separation distance d can be readily retrieved for a given ratio R. For a homogeneous medium (i.e., $\sigma_L \approx \sigma_d$), this relationship becomes an ideal case. For a heterogeneous medium (i.e., $\sigma_L \neq \sigma_d$), the ratio of conductivities $\sigma_L$ and $\sigma_d$ (i.e., $\sigma_L/\sigma_d$) must be taken into account. For example, the ratio of the conductivities $\sigma_L$ and $\sigma_d$ can be determined by taking an ex-vivo conductivity measurement longitudinally along sample spinal cord tissue to provide an estimate for the intra-lead conductivity $\sigma_L$, and taking an ex-vivo conductivity measurement transversely along the spinal cord tissue to provide an estimate for the cross-lead conductivity $\sigma_d$.

An accurate and representative reference data set for the field potential ratio R as a function of the separation distance d between the activated electrode $e_m$ and the measuring electrode $E_n$ (i.e., R(d)) can be obtained through conventional techniques, such as computational modeling, experiments on phantom models, or experiments on animal modes. For example with reference to FIG. 9, an example of a measured field potential ratio R (i.e., cross-lead vs. intra-lead) as a function of a cross-lead electrode separation distance d is shown. This data was obtained from a Finite Element Model (FEM) of a tripolar lead configuration for SCS. Such data may also be obtained computationally, empirically, or experimentally. As there shown, the ratio R is a monotonic function of the cross-lead electrode separation d, and thus, the inverse solution of the cross-lead electrode separation distance d is unique. Thus, for each value of the field potential ratio R, a corresponding cross-lead electrode separation distance d can be determined by either a look-up table or an explicit inverse function.

Figure 9:
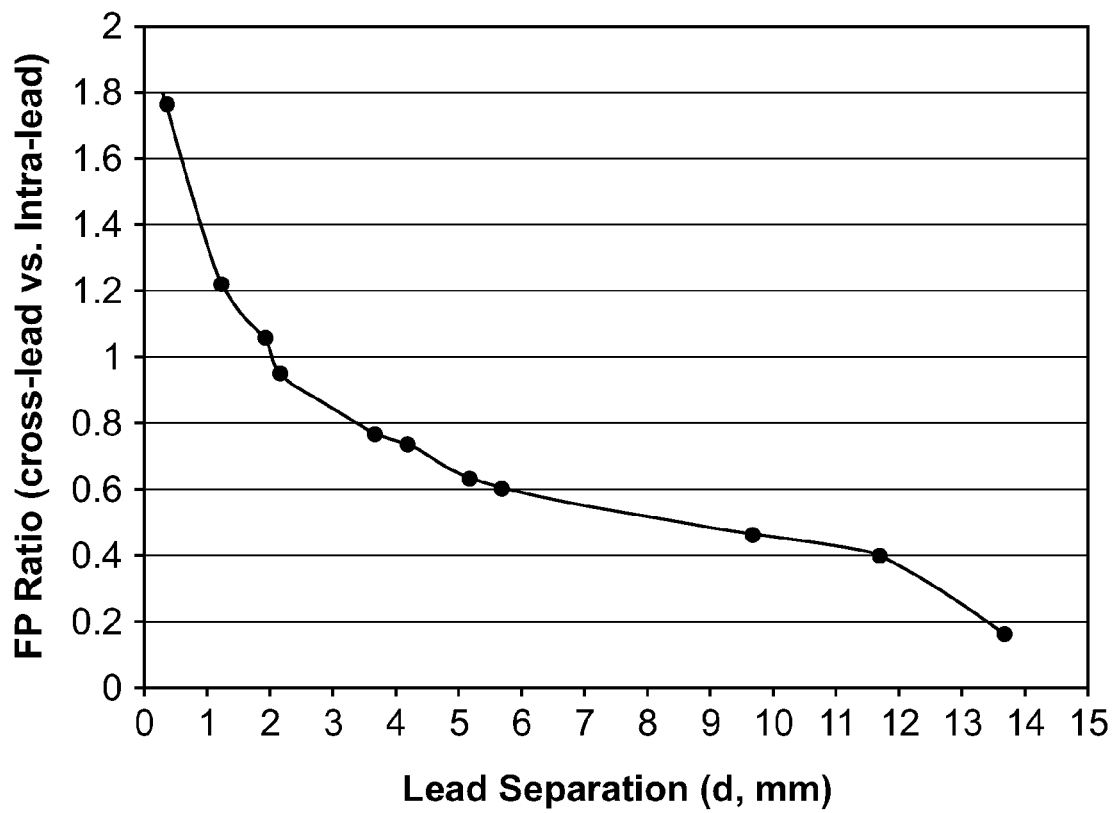
FIG. 9 is a plot of measured cross-lead versus intra-lead field potential measurements as a function of separation distance between electrodes carried by the two neurostimulation leads of FIG. 8.
Figure 10:
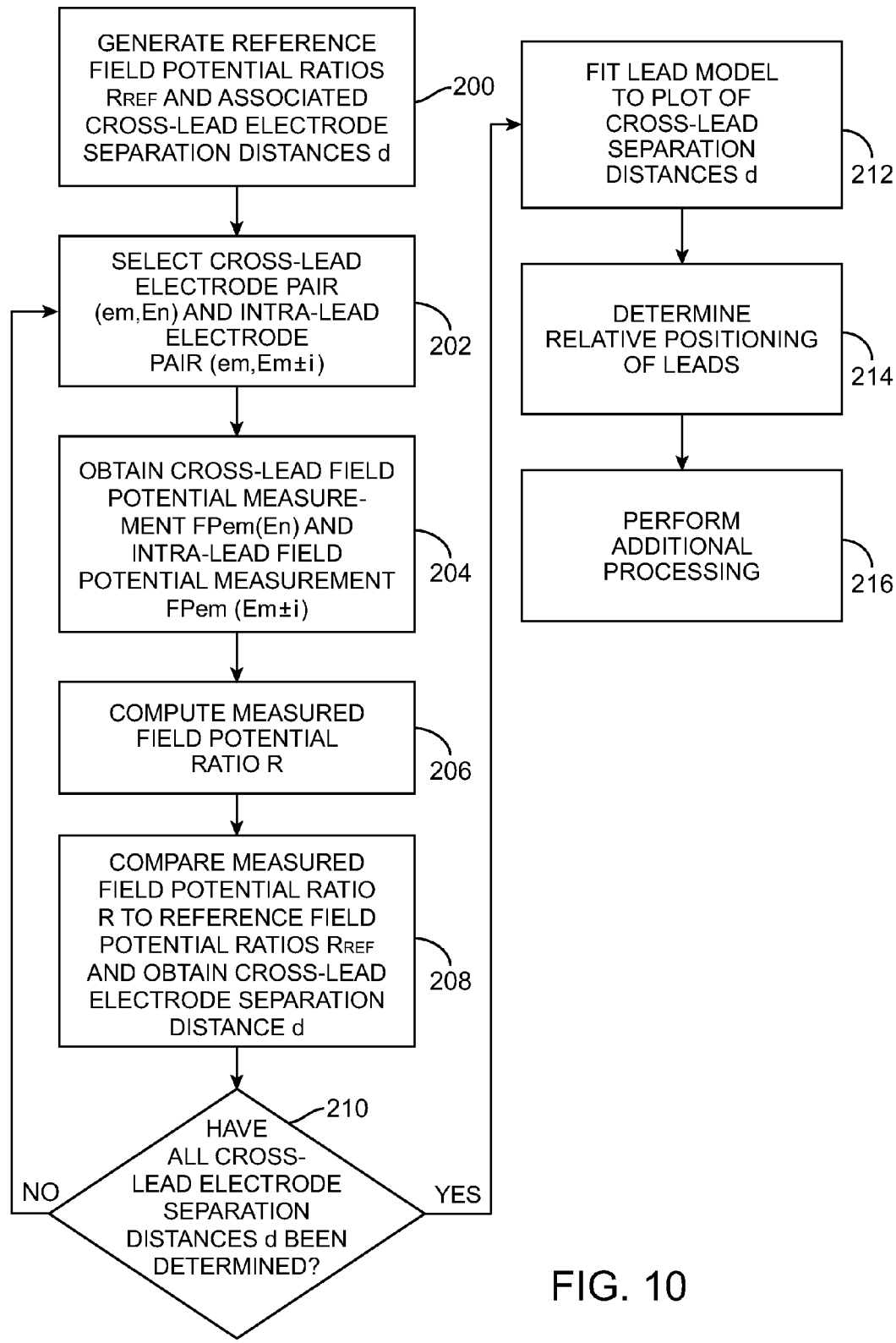
FIG. 10 is a flow diagram showing the process used by the CP of the SCS system of FIG. 1 to determine the relative positioning of the neurostimulation leads shown of FIG. 8.

As briefly discussed above, the relative positioning between two percutaneous leads 12 can be determined based on the separation distances between pairs of cross-lead electrodes. In particular, and with reference to FIG. 10, reference data in the form of a look-up table that includes reference field potential ratios $R_{REF}$ and associated cross-lead electrode separation distances d can be generated at step 200. An exemplary look-up table generated from the field potential ratios R versus lead separation data d of FIG. 9 is shown in FIG. 11. The reference field potential ratios $R_{REF}$ can be stored in the memory 130 of the processor 128 (see FIG. 7). Alternatively, instead of using reference field potential ratios $R_{REF}$, a reciprocal of the reference field potential ratios $R_{REF}$ and associated cross-lead electrode separation distances d can be stored in a look-up table. In either case, a ratio between the measured cross-lead field potential and the measured intra-lead field potential (either the measured cross-lead field potential divided by the measured intra-lead field potential or the measured intra-lead field potential divided by the measured cross-lead field potential) is computed.

Next, the cross-lead electrodes [$e_m$, $E_n$] and intra-lead electrodes [$e_m$, $E_{m\pm i}$] that are to be used to generate and measure the electrical fields (i.e., one cross-lead electrode pair and one intra-lead electrode pair) are selected at step 202. The variable i can be 1, 2, 3, 4, etc, or any number, as long as the distance between the intra-lead electrodes is known. Preferably, however, the variable i is 1 to minimize errors in the calculation. Thus, an electrode carried by one of the leads is selected as the activated electrode, an electrode carried by another one of the leads is selected as the cross-lead measurement electrode, and an electrode carried by the same lead that carries the activated electrode is selected as the intra-lead measurement electrode. Preferably, the intra-lead measurement electrode is immediately adjacent the activated electrode (i.e., directly above or directly below the activated electrode), and the cross-lead measurement electrode is immediately adjacent (or across) from the activated electrode. For example, as discussed above with respect to FIG. 8, electrodes E4 and E11 can be selected as the cross-lead electrode pair, and electrodes E4 and E5 or electrodes E4 and E3 can be selected as the intra-lead electrode pair. In some cases, the leads may be longitudinally staggered, and therefore, the cross-lead electrodes may not necessarily be those that would be directly across from each other in the case where the leads are longitudinally aligned. For example, if the leads illustrated in FIG. 8 were not longitudinally staggered, electrodes E4 and E12 would be selected as the cross-lead electrodes. However, due to a longitudinal stagger of one electrode, electrodes E4 and E11 are selected.

In the case where the leads are longitudinally staggered, the pair of electrodes that are respectively selected as the activated electrode and the cross-lead measurement electrode preferably have the least amount of longitudinal stagger in order to minimize any error in determining the separation distance d between the cross-lead electrodes. To make this determination, it will be necessary to determine the longitudinal stagger of the respective leads. This longitudinal lead stagger may be determined using conventional means, such as fluoroscopy, or may be performed electronically using techniques described in U.S. patent application Ser. No. 11/557,484, entitled "System and Method for Computationally Determining Migration of Neurostimulation Leads," or U.S. Pat. No. 6,993,384, entitled "Apparatus and Method for Determining the Relative Position and Orientation of Neurostimulation Leads," which are expressly incorporated herein by reference. Once the longitudinal lead stagger is determined, the cross-lead electrode pair can be selected either manually (e.g., user input into the CP 18) or automatically by the CP 18.

After the cross-lead electrode pair and the intra-lead electrode pair are selected, the cross-lead electrode pair is operated to generate and measure the electrical field to obtain a cross-lead field potential measurement $FP_{em}(E_n)$, and the intra-lead electrode pair is operated to generate and measure the electrical field to obtain an intra-lead field potential measurement $FP_{em}(E_{m\pm 1})$ at step 204. The CP 18 can perform this step by transmitting appropriate control data to the IPG 14 to initiate generation of the electrical field via the analog output circuitry 60 and measuring of the field potentials via the monitoring circuitry 70 (see FIG. 4). This field potential data can then be telemetered from the back telemetry circuitry 88 of the IPG 14 to the telemetry circuitry 134 of the CP 18 (see FIG. 7). Such control data and measured field potential data may be transmitted between the CP 18 and the IPG 14 via the telemetry circuitry 118 of the RC 16 (see FIG. 6).

Next, the ratio R between the cross-lead field potential measurement $FP_{em}(E_n)$ and the intra-lead field potential measurement $FP_{em}(E_{m\pm i})$ is computed at step 206. Then, at step 208, the separation distance d between the electrodes of the currently selected cross-lead electrode pair [$e_m$, $E_n$] is estimated by accessing the look-up table, and obtaining the separation distance d corresponding to the reference ratio $R_{REF}$ that is closest in value to the measured ratio R. Notably, utilizing a field potential measurement ratio R, as opposed to utilizing an absolute field potential measurement, minimizes the subject-to-subject variation or day-to-day variation (for a single subject) of tissue conductivities.

Next, at step 210, it is determined whether the separation distances d for all of the cross-lead electrode pairs have been determined. If not, the process returns to steps 202-208 in order to estimate the separation distance d between the electrodes of another cross-lead electrode pair, using the electrodes of another intra-lead pair as a reference. If the separation distances d for all of the cross-lead electrode pairs have been determined, a lead model is fitted to the separation distances d with respect to the longitudinal electrode positions at step 212. While any curve may be fit to the separation distance values d (including no fit), in a preferred embodiment, with a simple assumption of the lead as relatively rigid and straight, a straight line can be fit to the separation distance values d using a linear function.

Figure 12:
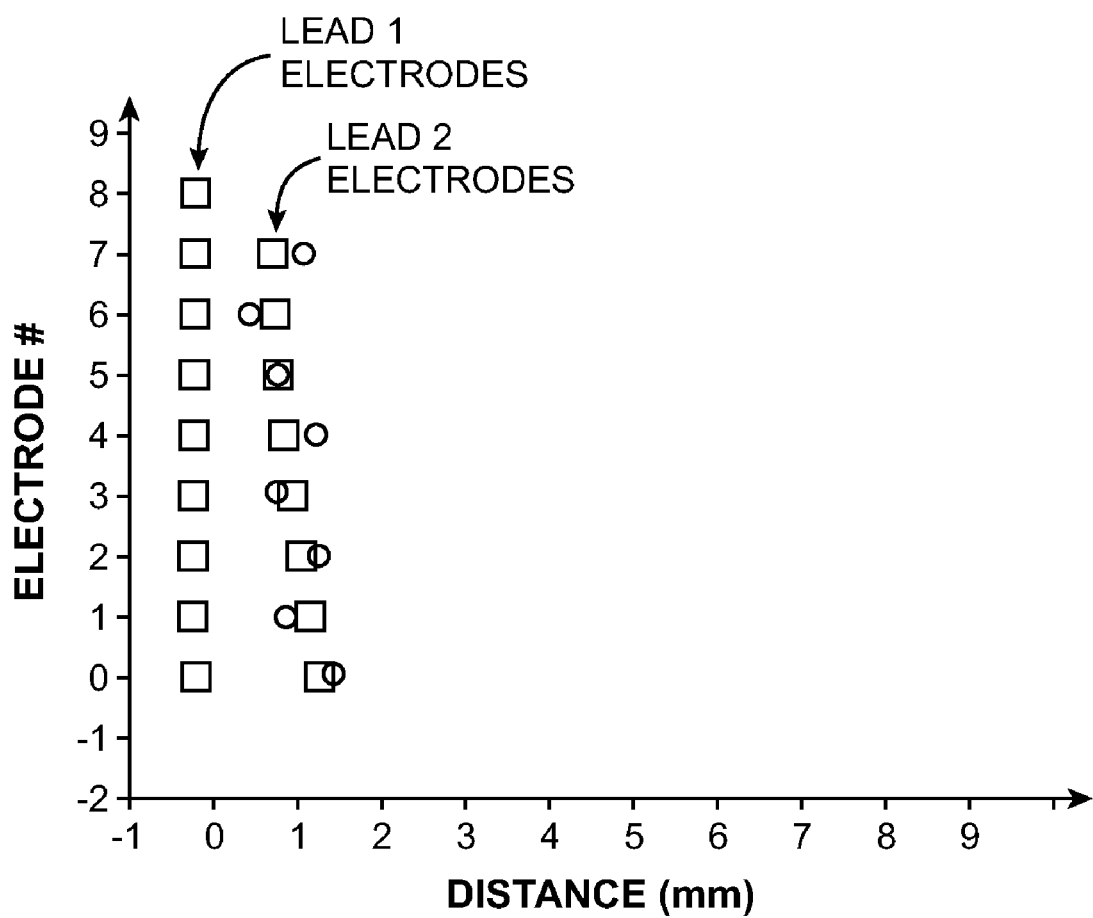
FIG. 12 is a plot of distance values calculated by the CP and a model of a lead fitted to the distance values.

Candidate fitting methods include, but are not limited to, curve fitting and regression. An alternative embodiment can fit a simple curve to the plotted separation distance values d. This may be clinically meaningful, since percutaneous leads are often not rigid and straight, and may curve within the body space. A simple curve applied to the plotted separation distance values d may be used to represent this physical reality. An exemplary set of cross-lead separation distances values d and a fitted straight line lead model is illustrated in FIG. 12. As there shown, a model of lead electrodes (represented by squares) arranged in a straight line is fitted to plotted separation distance values d (represented by circles). Notably, the fitting process may balance out the variance in the estimation of the pair-wise cross-lead electrode separation distances d. Reciprocal measurements (e.g., using electrode E11 as an activating electrode, electrode E4 as a cross-lead field potential measurement electrode, and E12 or E10 as an intra-lead field potential measurement electrode) can be used to increase the confidence of the fitting process.

Once the lead model is fitted to the cross-lead electrode separation distance values d, the relative positioning (e.g., the distance between the leads and/or the angle between the leads) can be estimated at step 214. As shown in FIG. 12, representations of first lead electrodes (represented by squares) are disposed vertically along a reference distance of 0 mm, and representations of the second lead electrodes (represented by squares), which were fitted to the plotted separation distances d, are longitudinally offset in the caudal direction relative to the first lead electrodes. The distal tip of the second lead is separated from the first lead by approximately 1 mm, and the bottom tip of the second lead is separated from the first lead by approximately 1.5 mm, which provides dimensions that can be used to obtain the relative angle between the leads using conventional geographical techniques. Notably, the quantitative information of the relative lead position obtained at step 214 can also be used to refine the estimation of the longitudinal offset between the leads.

This quantitative information can also be used to detect the retrograde condition of one of the paired leads (i.e., when one lead is oriented in the rostral direction while the other is oriented in caudal direction). For example, when such retrograde condition is unknown, one would assume that, e.g., electrodes E1 and E9 are aligned (i.e., adjacent to each other), so that the separation distance d estimated between them is reasonable. However, if one of the leads are actually retrograde, but this condition is not detected (which could happen if one looks only at the fluoroscopy image to determine the stagger), electrode E1 may be adjacent electrode E16, and electrode E9 is much further away from electrode E1, such that the distance estimated between electrodes E1 and E9 are unusually large, which may suggest a retrograde condition.

Additional processing, such as displaying the leads and their proper positioning relative to each other (e.g., on the 124 of the CP 18 (shown in FIG. 3), can be performed at step 216, so that the user may either reposition the leads or appropriately program the IPG 14 taking into account the relative positioning. Thus, it can be appreciated that because this method is electric field based and automatic, it can potentially reduce or minimize the need for fluoroscopy. In the case where more than two leads are used (e.g., in a tri-lead arrangement), such additional processing can further include using the pair-wise lead separation to distinguish the middle and lateral leads from each other.

That is, since the separation between two lateral leads would be greater than that between a middle lead and a lateral lead, or that between two middle leads, a relatively large separation distance d between two leads would indicate that these two leads are lateral leads, with the remaining lead being determined as the middle lead by the process of elimination. In this case, the CP 18 may be configured for remapping the outputs (i.e., the ports) of the analog output circuitry 60 (shown in FIG. 4) to the proper electrodes 26 of the stimulation lead or leads 12 by transmitting appropriate control data to the IPG 14. Once the middle lead 12 is identified and the outputs of the analog output circuitry 60 are mapped to the electrodes 26, the CP 18 can then generate stimulation parameters for use by the IPG 14. Thus, the user may insert each lead 12 into any port 44 of the connector 42 of the IPG 14 without concern that the incorrect connector port is being used.

While the present inventions contemplate that the CP 18 may, itself, process or analyze the measured field potential information in order to effect determination of the relative positioning of multiple leads, as well as to effect the identification of the leads in a tri-polar lead arrangement, the IPG 14 or the RC 16 may optionally have this capability. If the IPG 14, alone, performs these functions, it may modify its own programming and remap its own ports without communication with the CP 18 or the RC 16. In this case, the RC 16 and/or CP 18 may conventionally operate with respect to the IPG 14.

As previously stated, other electrical parameters besides field potential can be used to estimate the cross-lead separation distances. For example, a cross-lead bipolar impedance measurement and a reference intra-lead bipolar impedance measurement can be taken (using an electrode pair as an anode and a cathode and applying a constant current to take an impedance measurement on one of the electrodes). The measured impedance will be proportionate to the field potential drop between the electrode pair. The larger the bipolar impedance is, the larger the distance between the electrode pair.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of operating two leads disposed adjacent tissue of a patient, the method comprising:

activating a first one of a pair of electrodes respectively carried by the two leads to generate an electrical field within the tissue;

measuring an electrical parameter in response to the generated electrical field at a second one of the pair of electrodes;

measuring a reference electrical parameter in response to the generated electrical field at a reference electrode carried by the same one of the two leads that carries the first electrode, wherein a reference distance between the first electrode and the reference electrode is known prior to the generation of the electrical field;

computing a ratio between the measured electrical parameter and the measured reference electrical parameter; and computing a distance between the pair of electrodes as a function of the computed ratio and the reference distance.

2. The method of claim 1, wherein the measured electrical parameter is a measured field potential of the generated electrical field.

3. The method of claim 1, wherein the measured electrical parameter is a measured impedance.

4. The method of claim 1, wherein the ratio is computed by dividing the measured electrical parameter by the measured reference electrical parameter.

5. The method of claim 1, further comprising determining the relative positioning between the two leads at least partially based on the computed distance.

6. The method of claim 5, wherein the relative positioning is the distance between the two leads.

7. The method of claim 5, wherein the relative positioning is the angle between the two leads.

8. The method of claim 5, further comprising activating a third one of another pair of electrodes respectively carried by the two leads to generate another electrical field within the tissue, repeating the electrical parameter measuring at a fourth one of the other pair of electrodes, repeating the reference electrical parameter measuring at another reference electrode, and repeating the ratio computing and distance computing steps to determine another distance between the other pair of electrodes.

9. The method of claim 8, further comprising:
plotting the distances; and
fitting a lead model to the plotted distances, wherein the relative positioning between the two leads is determined based on the fitted lead model.

10. The method of claim 1, wherein three leads are operated, the three leads including a middle lead and a pair of leads flanking the middle lead, the method further comprising identifying the middle lead based on the computed distance.

11. The method of claim 1, further comprising determining a longitudinal stagger between the two leads, and selecting the pair of electrodes having the least amount of longitudinal stagger based on the determined longitudinal stagger.

12. The method of claim 1, further comprising displaying the relative positioning of the two leads based on the computed distance.

13. The method of claim 1, further comprising programming a neurostimulator with a plurality of stimulation parameters based on the computed distance.

14. The method of claim 1, wherein the tissue is spinal cord tissue.

15. A medical system, comprising:
a first lead configured for being placed adjacent tissue of a patient, the first lead carrying a first electrode and a reference electrode;
a second lead configured for being placed adjacent the tissue of the patient, the second lead carrying a second electrode;
a controller configured for activating the first electrode to generate an electrical field within the tissue;
monitoring circuitry configured for measuring an electrical parameter in response to the generated electrical field at the second electrode, and measuring a reference electrical parameter in response to the generated electrical field at the reference electrode, wherein a reference distance between the first electrode and the reference electrode is known prior to generation of the electrical field; and
at least one processor configured for computing a ratio between the measured electrical parameter and the measured reference electrical parameter, and computing a distance between the first and second electrodes as a function of the computed ratio and the reference distance.

16. The medical system of claim 15, wherein the measured electrical parameter is a measured field potential of the generated electrical field.

17. The medical system of claim 15, wherein the measured electrical parameter is a measured impedance.

18. The medical system of claim 15, wherein the at least one processor is configured for computing ratio by dividing the measured electrical parameter by the measured reference electrical parameter.

19. The medical system of claim 15, wherein the at least one processor is configured for determining the relative positioning between the two leads at least partially based on the computed distance.

20. The medical system of claim 19, wherein the relative positioning is the distance between the two leads.

21. The medical system of claim 19, wherein the relative positioning is the angle between the two leads.

22. The medical system of claim 21, wherein the first lead carries a third electrode and another reference electrode, and the second lead carries a fourth electrode, wherein the controller is configured for activating the third electrode to generate another electrical field within the tissue, the monitoring circuitry is configured for repeating the electrical parameter measuring and the reference electrical parameter measuring with respect to the fourth electrode and the other reference electrode, and the at least one processor is configured for performing the ratio computing and distance computing to determine another distance between the third and fourth electrodes.

23. The medical system of claim 22, wherein the at least one processor is configured for plotting the first and second distances, fitting a straight line or a curve to the first and second plotted distances, and determining the relative positioning between the two leads based on the fitted straight line or curve.

24. The medical system of claim 15, further comprising a third lead configured for being placed adjacent tissue of a patient, wherein the first, second, and third leads are configured to be arranged as a middle lead and two leads flanking the middle leads, the at least one processor configured for identifying the middle lead based on the computed distance.

25. The medical system of claim 15, wherein the at least one processor is configured for determining a longitudinal stagger between the two leads, and selecting the first and second electrodes having the least amount of longitudinal stagger based on the determined longitudinal stagger.

26. The medical system of claim 15, further comprising a monitor configured for displaying the relative positioning of the two leads based on the computed distance.

27. The medical system of claim 15, further comprising a neurostimulator, wherein the at least one processor is configured for programming the neurostimulator with a plurality of stimulation parameters based on the computed distance.

28. The medical system of claim 15, further comprising an implantable device and an external device, wherein the implantable device contains the controller, and the external control device contains one or more of the at least one processor.

* * * * *